United States Patent [19]

Krapf

[11] Patent Number: Plant 6,689

[45] Date of Patent: Mar. 21, 1989

[54] APPLE TREE: ARLET

[75] Inventor: Bernhard Krapf, Rapperswill, Switzerland

[73] Assignee: Swiss Federal Research Station, Wadenswil, Switzerland

[21] Appl. No.: 96,980

[22] Filed: Sep. 15, 1987

[51] Int. Cl.[4] ..... A01H 5/03

[52] U.S. Cl. ..... Plt./34

[58] Field of Search ..... Plt./34

*Primary Examiner*—Robert E. Bagwill

*Attorney, Agent, or Firm*—Klarquist, Sparkman, Campbell, Leigh & Whinston

[57] ABSTRACT

A new variety of apple tree has fruit with a firm flesh which is excellent for fresh eating and for use in salads. The fruit of the variety also exhibits a relatively long shelf life when compared with Golden Delicious apples and takes on a somewhat waxy or greasy appearance after extended storage. The new variety produces high and regular fruit yields and has fruit with medium fruit ripening.

1 Drawing Sheet

The present invention relates to a new and distinct variety of apple tree which I call "Arlet". This new variety was originated by me from a cross between Golden Delicious apple and the Idared apple made at the Swiss Federal Research Station in Wadenswill, Switzerland.

The cross which resulted in my new variety was performed in 1958. The resulting tree was grown in a cultivated area. The first fruit from my new variety was harvested in 1968. Because of the regular crops and high quality fruit produced from my new variety, in 1972 it was asexually propagated in larger numbers in Switzerland for further testing. Fruit from my new variety was thereafter sold in Europe and was favorable received. The positive results from testing of the tree and fruit prompted the commercial release of this tree in Europe during the 1970's. To my knowledge, my new variety has not previously been offered for sale or made publicly available in the United States of America. However, in the winter of 1984–1985, budwood from my new variety was sent to nurseries in Woodburn, Oreg. and in Orando, Wash. for test purposes. This budwood was grafted onto one-year old apple trees at the Orando, Wash. site, which produced some fruit for harvest in mid-September 1986. This testing confirmed that my Arlet variety of apple tree is suitable for apple growing regions of the United States of America.

Close examinations of the parent Arlet apple tree and of its progeny produced asexually both in Switzerland, and under test in the states of Oregon and Washington, have convinced me that my new variety is distinguished from all other apple varieties of which I am aware, as evidenced by the following unique combination of characteristics, which are firmly fixed, and which are transmitted through succeeding propagations:

(1) Fruit with a firm flesh that is excellent for fresh eating and use in salads;
(2) Fruit with a relatively long shelf life when compared with Golden Delicious apples, but which takes on a somewhat "waxy" or "greasy" appearance after extended storage;
(3) A high and regular fruit yield (like the Jonagold variety) which typically requires fruit thinning for best production and may require two harvests for optimum fruit color; and (4) A relatively early fruit maturation (Typically between Spartan and Jonagold varieties in Switzerland).

The accompanying illustration shows typical specimens of the foliage and fruit of my new variety of apple tree, depicted in color as nearly true as it is reasonably possible to make the same in a color illustration of this character. In this illustration, certain of the fruit specimens are shown in both elevation and in plan views to disclose the exterior details thereof, and another fruit specimen is shown in transverse cross-section to disclose the interior details.

The following is a detailed description of my new apple tree with color terminology in accordance with The Royal Horticultural Society Colour Chart, except where ordinary dictionary significance of color is indicated.

Variety: Arlet.

Parentage:
- *Seed parent.*—Golden Delicious.
- *Pollen parent.*—Idared.

Locality where grown and observed: Wadenswill, Switzerland; Orando, Wash.; and Woodburn, Oreg.

Dates of first and last pickings: Time of fruit ripening, medium, usually between Spartan and Jonagold varieties in Wadenswill, Switzerland.

Tree:
- *Vigor.*—Initially strong, later medium, fruits also on one-year old shoots.
- *Habit.*—Slightly dropping.
- *Fruit.*—Well distributed.
- *Leaf.*—Medium size; somewhat U-folded; ovate; medium density; apex acutely drawn and twisted; rather dark green in color; finely serrate margin.

Flowering period and pollinators: Mid-early flowering (typically early to mid-May in Wadenswill, Switzerland); suitable as a pollinator; pollinators of my new variety include Berlepsch, Idared, Maigold, Glockenapfel, Jonathan, Golden Delicious, Gloster and Red Delicious.

Fruit:
- *Size.*—Medium to large.
- *Shape.*—Slightly oblong and conical, symmetric.

*Cavity.*—Medium wide, medium deep.

*Basin.*—Medium wide, medium deep, often russeted, slightly ripped.

*Calyx.*—Medium, closed.

*Skin.*—Smooth, slightly tough, somewhat greasy, bruise resistant.

*Color.*—Ground color — yellow (like RHS 20A).

*Overcover.*—50% red, solid flush (like RHS 46-B).

*Lenticels.*—Sharp, painted.

*Stem.*—25–30 mm long, medium thickness, light brown.

*Locules (carpels).*—Medium, heart-shaped; kidney-shaped compartments, oblong pips.

*Quality.*—Flesh of the fruit is yellowish, firm with a fine texture, very juicy, medium content of sugar and acidity, pH 3.4 (at harvest); flavour of the fruit is fresh, fine, sometimes slightly waxy; well suitable for processing.

*Shelf-life.*—Long in comparison with Golden Delicious apples which tend to shrivel unless placed in plastic bags.

*Storage.*—In cold-storage-until end of March (2–3 degrees C.); in CA-storage until end of May (4 degrees C., 3% $CO_2$, 3% $O_2$); hardly any storage disease; tends to become "greasy" or "waxy" after extended cold storage. Greasiness can be suppressed by CA-storage.

*Production.*—High and regular yields (like Jonagold); fruit thinning is typically required for best production; for optimum color and to provide sufficient sun for ripening, two harvests may be necessary.

Resistance to disease: Medium susceptibility to mildew, susceptibility to apple scab (*Venturia inacqualis*) like Golden Delicious.

Use: Like Golden Delicious, particularly good for fresh eating and in salads.

I claim:

1. A new and distinct variety of apple tree, substantially as herein shown and described, characterized by its fruit with firm flesh, fruit with a relatively long shelf life, but which takes on a somewhat waxy or greasy appearance after extended storage, time of fruit ripening — medium, high and regular fruit yields.

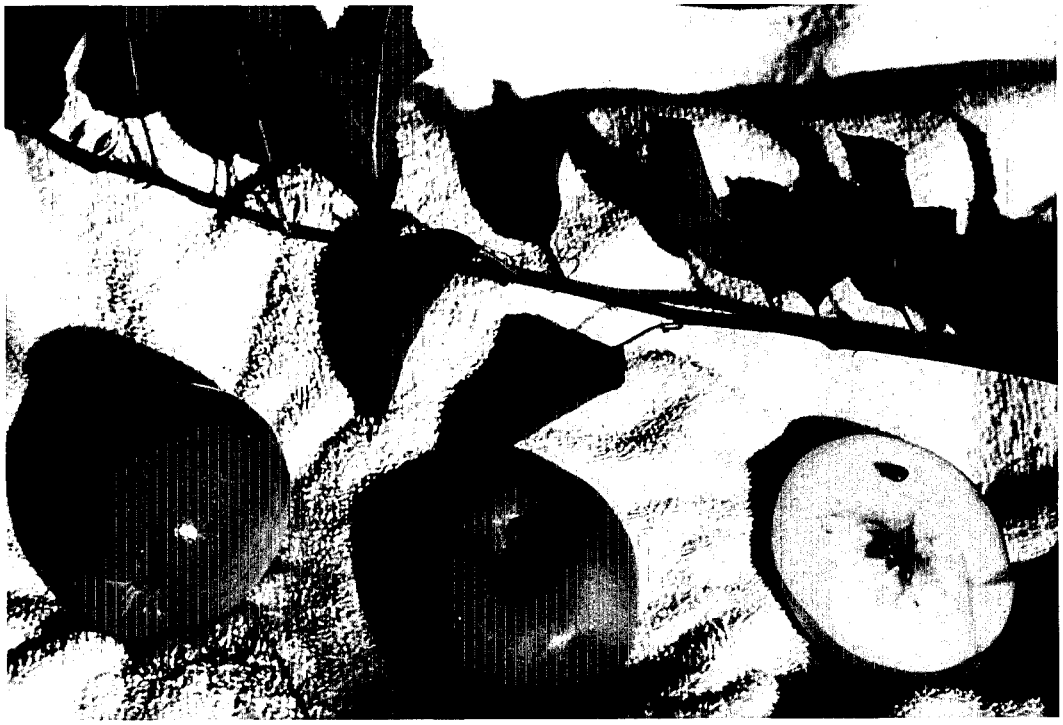
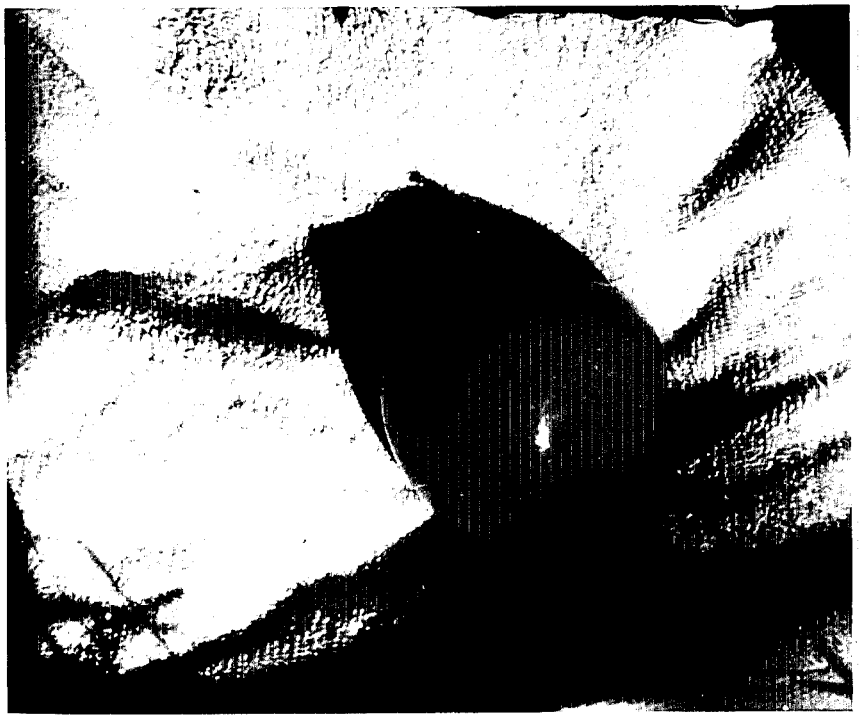

* * * * *